United States Patent [19]
Cooke et al.

[11] 3,978,086
[45] Aug. 31, 1976

[54] 2-AMINO-4,5-METHYLENEDIOXYPHENYL NITRILES

[75] Inventors: George A. Cooke, Denville; William J. Houlihan, Mountain Lakes, both of N.J.

[73] Assignee: Sandoz, Inc., E. Hanover, N.J.

[22] Filed: Jan. 27, 1975

[21] Appl. No.: 543,983

Related U.S. Application Data

[62] Division of Ser. No. 351,092, April 13, 1973, Pat. No. 3,876,665, which is a division of Ser. No. 140,990, May 6, 1971, Pat. No. 3,748,342.

[52] U.S. Cl. .............................................. 260/340.5
[51] Int. Cl.² ...................................... C07D 317/44
[58] Field of Search ............................ 260/340.5 R

[56] References Cited
UNITED STATES PATENTS

| | | | |
|---|---|---|---|
| 3,801,601 | 4/1974 | Reinhold et al. | 260/340.5 |
| 3,850,962 | 11/1974 | Grunberg et al. | 260/340.5 |

OTHER PUBLICATIONS

Chem. Abstracts: 77:151836t.

*Primary Examiner*—Ethel G. Love
*Attorney, Agent, or Firm*—Gerald D. Sharkin; Richard E. Vila

[57] ABSTRACT

2-Amino-4,5-methylenedioxyphenyl nitriles are useful as intermediates for 2-amino-4,5-methylenedioxybenzophenonimines when reacted with a phenyl lithium or phenyl magnesium halide.

1 Claim, No Drawings

2-AMINO-4,5-METHYLENEDIOXYPHENYL NITRILES

This is a division of application Ser. No. 351,092, filed Apr. 13, 1973 now U.S. Pat. No. 3,876,665, which in turn is a division of application Ser. No. 140,990, filed May 6, 1971 now U.S. Pat. No. 3,748,342.

This invention relates to 2(1H)-quinazolinone derivatives. More particularly, this invention provides processes for preparing compounds of formula I:

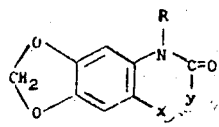

in which
R signifies an alkyl radical of 1 to 5 carbon atoms, e.g., methyl, ethyl, isopropyl and t-butyl; cyclo(lower)alkyl of 3 to 6 carbon atoms, e.g., cyclopropyl and cyclohexyl; or cyclo(lower)alkyl(lower) straight chain alkyl of 4 to 7 total carbon atoms in which the cycloalkyl is of 3 to 6 carbon atoms and the straight chain alkyl is of 1 to 3 carbon atoms, e.g., cyclopropylmethyl; and
x y signifies a group

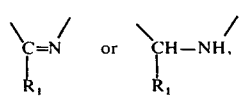

in which
$R_1$ signifies a radical of formula II:

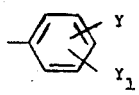

or of formula III:

in which either Y and $Y_1$ are the same or different and signify a hydrogen, fluorine or chlorine atom, an alkyl or alkoxy radical of 1 to 3 carbon atoms, or a nitro or trifluoromethyl group, provided that no more than one of Y and $Y_1$ signifies a trifluoromethyl or nitro group;
or Y and $Y_1$ are on adjacent carbon atoms and together signify a methylenedioxy group, and
$Y_2$ signifies a hydrogen, fluorine or chlorine atom, or an alkyl radical of 1 to 3 carbon atoms.

The processes of this invention are characterised by
a. producing a compound of formula Ia,

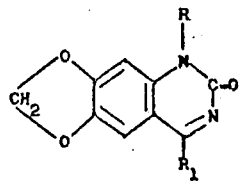

in which R and $R_1$ are as defined above, by cyclising a compound of formula IV,

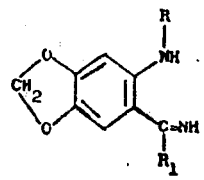

in which R and $R_1$ are as defined above, with phosgene, or b. producing a compound of formula Ib,

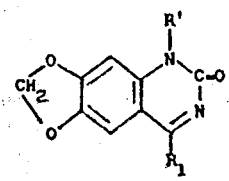

in which $R_1$ is as defined above, and
R' has the same significance as R, defined above, except that it may not signify a tertiary alkyl group in which the tertiary carbon atom is directly attached to the ring nitrogen atom,
by cyclising a compound of formula IVa,

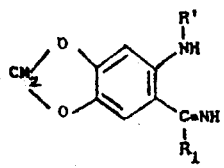

in which R' and $R_1$ are as defined above,
with a carbonic acid derivative selected from the group consisting of
 i. a $C_{1-2}$ alkyl chlorocarbonate,
 ii. a $C_{1-5}$ alkyl carbamate, and
 iii. 1,1'-carbonyldiimidazole,
  provided that when a $C_{1-5}$ alkyl carbamate is employed, the reaction is effected at a temperature of at least 140°C, or
c. producing a compound of formula Ib, stated above, by cyclising a compound of formula Va.

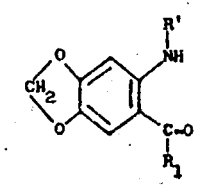

in which R' and $R_1$ are as defined above,
with a carbamic acid derivative selected from the group consisting of
 i. a $C_{1-5}$ alkyl carbamate,
 ii. urea, and
 iii. carbamyl chloride,
at an elevated temperature, provided that when a $C_{1-5}$ alkyl carbamate is employed, the process is effected at a temperature of at least 140°C. and in the presence of a catalytic amount of a Lewis acid, or d. producing a compound of formula Ia, stated above, by cyclising a compound of formula V,

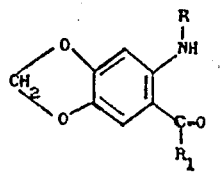   V in which R and $R_1$ are as defined above,
either (i) by reaction with an acid chloride or bromide and an isocyanate of formula VI, $$M - N = C = O \qquad VI$$

in which M signifies an alkali metal or alkaline earth metal cation, or the ammonium cation,
or with the reaction product of an acid chloride or bromide and an isocyanate of formula VI, stated above,
or (ii) with isocyanic acid, or e. producing a compound of formula Ic

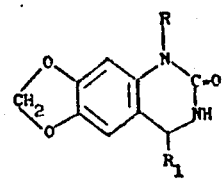   Ic in which R and $R_1$ are as defined above,
by cyclising a compound of formula VII,

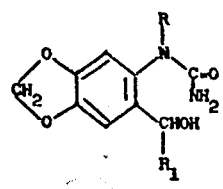   VII in which R and $R_1$ are as defined above,
by removal of the elements of water, or f. producing a compound of formula Id.

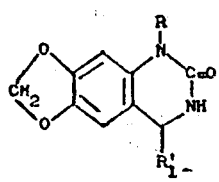   Id in which R is as defined above, and
$R_1'$ has the same significance as $R_1$, defined above, except that it may not signify a phenyl radical having a nitro substituent,
by reacting a compound of formula VIII

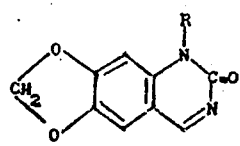   VIII in which R is as defined above,
with a compound of formula IX, $$R'_1 Q \qquad IX$$

in which $R'_1$ is as defined above, and
Q signifies a lithium atom or a radical —MgX'', in which X'' signifies a chlorine or bromine atom,
in the presence of an organic solvent which is inert under the reaction conditions, and hydrolysing the resulting product, or g. producing a compound of formula Ic, stated above, by reducing a compound of formula Ia, stated above, or h. producing a compound of formula Ib, stated above, by reacting a compound of formula X,

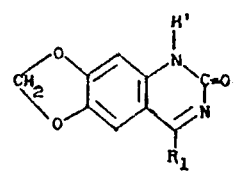   X in which $R_1$ is as defined above, and
M' signifies an alkali metal atom,
with a compound of formula XI, $$R'X' \qquad XI$$

in which R' is as defined above,
and X' signifies a chlorine, bromine or iodine atom, in the presence of an organic solvent which is inert under the reaction conditions, or i. producing a compound of formula Ie, Ie in which $R_1'$ is as defined above,
by oxidizing a compound of formula XII,

XII in which $R_1'$ and X' are as defined above,
or a compound of the formula XIII

XIII in which $R_1'$ is as defined above, or j. producing a compound of formula Ib, stated above, by reacting a compound of formula XIV,

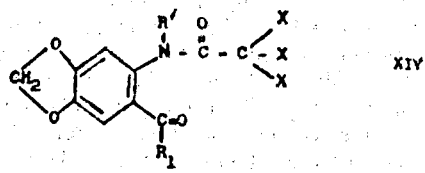

in which R' and $R_1$ are as defined above, and X signifies a fluoro, chloro or bromo atom, with ammonia.

k. producing a compound of the formula Ia by hydrolyzing a compound of the formula XV

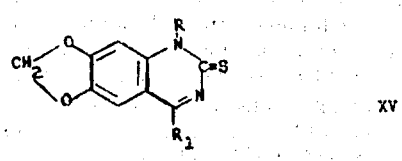

in which R and $R_1$ are as defined above, at a temperature of 10° to 150°C., or l. producing a compound of the formula Ia by oxidizing a compound of the formula XVI,

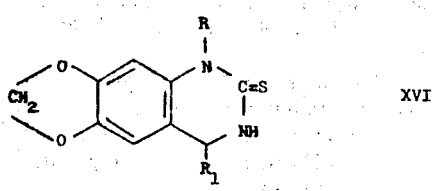

in which R and $R_1$ are as above defined, or m. producing a compound of the formula If

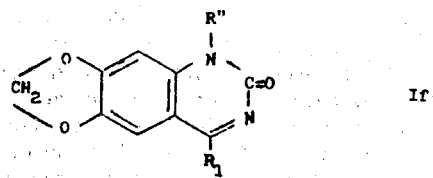

in which $R_1$ is as defined above
R'' signifies cyclo(lower)alkyl of 3 to 6 carbon atoms or cyclo(lower)alkyl(lower)straight chain alkyl of 4 to 7 total carbon atoms (as previously defined) by subjecting a corresponding compound of the formula Ig

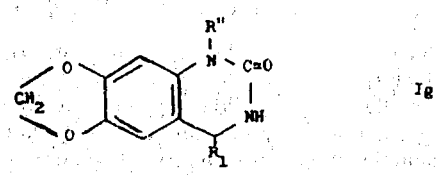

in which $R_1$ and R'' are as defined, to oxidation in an organic solvent, or n. producing a compound of the formula Ig, above, by reacting a compound of the formula XVII

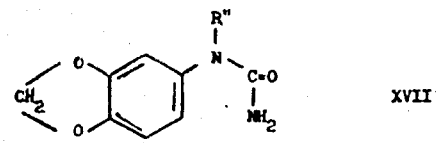

with a compound of the formula XVIII

$R_1CHO$            XVIII wherein $R_1$ and R'' are as defined, at elevated temperatures.

Process (a) is suitably carried out at a temperature of from 0° to 50°C., preferably 10° to 30°C. The reaction may be carried out in an organic solvent which is inert under the reaction conditions, suitably an aromatic hydrocarbon, e.g. benzene, toluene, and xylene, preferably benzene. The mole ratio of phosgene to the compound of formula IV is not particularly critical but a substantial excess of phosgene is preferably employed. The process may optionally be carried out in the presence of an acid-binding agent such as an inorganic base, e.g. sodium or potassium carbonate, or a tertiary amine, e.g. a trialkylamine or pyridine, preferably triethylamine.

Process (b) (i) involving reaction of a compound of formula IVa with methyl chlorocarbonate or ethyl chlorocarbonate, preferably ethyl chlorocarbonate, may suitably be carried out at a temperature of from 30° to 150°C., preferably 60° to 100°C. The reaction may be carried out in an organic solvent which is inert under the reaction conditions, suitably an aromatic hydrocarbon, e.g. benzene, toluene, and xylene, preferably benzene. Other suitable solvents include dioxane. The mole ratio of the chlorocarbonate to the compound of formula IVa is not critical but the reaction is preferably carried out with a substantial excess of the chlorocarbonate. The reaction time may, for example, range from ½ hour to 10 hours, more usually 1 to 4 hours. The cyclisation with the chlorocarbonate may be optionally carried out in the presence of an acid-binding agent such as an inorganic base, e.g. sodium carbonate or potassium carbonate, or a tertiary amine, e.g. a trialkylamine or pyridine, more preferably triethylamine.

Process (b) (ii) is suitably carried out at a temperature of from 140° to 200°C, preferably 160° to 180°C. The mole ratio of the alkyl carbamate, preferably urethane, to the compound of formula IVa is not critical. In the preferred forms of practice, there is employed a substantial excess of carbamate which also serves as the preferred solvent for the reaction. Other suitable high-boiling organic solvents which are inert under the reaction conditions may alternatively or additionally be employed, if desired. The reaction time may for example range for ½ to 10 hours, more usually 1 to 4 hours. The cyclisation with the carbamate is optionally and preferably conducted in the presence of a Lewis acid as catalyst for the reaction. The amount of Lewis acid employed is preferably between about 5% to 20% based on the weight of compound IVa in the reaction mixture. The preferred catalyst is zinc chloride.

Process (b) (iii) is suitably carried out at a temperature of from 20° to 120°C, preferably 60° to 90°C. The reaction is preferably carried out in an organic solvent which is inert under the reaction conditions, suitably an aromatic hydrocarbon, e.g. benzene, toluene or xylene, especially benzene. The mole ratio of 1,1'-carbonyldiimidazole to the compound of formula IVa is not particularly critical but an excess of 1,1'-carbonyldiimidazole is preferably employed.

Process (c)(i) is conveniently carried out at a temperature of from 140° to 200°C, the preferred Lewis acid being zinc chloride and the preferred carbamate being ethyl carbamate. If desired, the reaction may be carried out in an organic solvent which is inert under the reaction conditions, e.g. o-dichlorobenzene, but this is not necessary since an excess of the carbamate can be used for this purpose. Depending on the particular conditions employed, a suitable reaction time is from about 30 minutes to about 4 hours.

Process (c) (ii) is a reaction of known type and may, for example, be effected in manner analogous to that described in Japanese Pat. No. 20865/65, published Sept. 16, 1965. The process is conveniently effected at a temperature of from 140° to 220°C, preferably 180° to 210°C, and in the absence of added solvent.

Process (c) (iii) may be effected in similar manner to process (c) (ii).

Process (d) (i) is conveniently effected in an organic solvent which is inert under the reaction conditions, at a temperature of from 10° to 80°C, preferably 30° to 70°C. As indicated, the process may be effected by reacting a compound of formula V with the reaction product of an acid chloride or bromide and an isocyanate of formula VI, and it is generally preferred to first react the acid halide and compound of formula VI and then add the compound of formula V to the resulting reaction mixture. The reaction of the acid halide and compound VI is exothermic and is preferably initiated at a temperature of from 10° to 30°C. It will be understood that the acid halides employed should not carry substituents or functional groups which would interfere with the process. Suitable acid halides include acetyl chloride and benzoyl chloride, preferably benzoyl chloride. Naturally, the most suitable compounds of formula VI are those most readily reacting with the acid halide to eliminate as a by-product a halide of the cation M. Suitably, the compound of formula VI is an alkali metal isocyanate such as sodium isocyanate or ammonium isocyanate, and preferably ammonium isocyanate. Suitable solvents include lower alcohols, ketones and cyclic ethers, acetone being preferred.

Process (d) (ii) is suitably effected at a temperature of from 50° to 150°C, preferably 100° to 140°C. Isocyanic acid is well known to be unstable and is therefore desirably prepared in situ. Thus, the process may be effected in acidic medium employing a salt of isocyanic acid of formula VI stated above. The compound of formula VI is preferably an alkali metal, e.g. sodium or potassium salt or most preferably the ammonium salt. The acid employed to produce in situ the desired isocyanic acid from the compound of formula VI is preferably a lower carboxylic acid, desirably acetic acid, which may also be conveniently employed as a solvent for the reaction.

Process (e) is preferably carried out at an elevated temperature and under acidic conditions. Suitable temperatures are for example from 80° to 150°C, preferably 95° to 120°C. The acid employed in the dehydration is desirably a strong inorganic acid such as sulfuric acid or hydrochloric acid, or an organic acid such as acetic acid, more preferably the latter. Water may be employed as the sole reaction medium although various co-solvents, e.g. ethanol, may also be used, if desired or required to insure optimum solubility.

Process (e) is a reaction of a type described in the literature, for example, J. Chem. Soc. 1959, 3555.

Process (f) is preferably carried out at a controlled temperature of from −40° to +50°C, preferably +15° to +35°C, and usually most conveniently at about room temperature (20°C). The organic solvent which is inert under the reaction conditions is preferably an organic acyclic or cyclic ether such as diethyl ether, dimethoxyethane, tetrahydrofuran, or dioxane or a mixture of such ethers, more preferably a cyclic ether such as tetrahydrofuran. The mole ratio of the compound of formula IX to the quinazolinone of formula VIII is not particularly critical. In the more preferred forms of practice an excess of the magnesium halide or lithium compound is employed typically to provide a ratio of from about 3:1 to 30:1, more preferably from 5:1 to 20:1. Lithium compounds of formula IX are preferred. The reation time may for example range from 15 minutes to 5 hours. The reaction is desirably conducted under anhydrous conditions and followed by hydrolysis in manner known per se. The hydrolysis may for example be effected by addition of water to the resulting reaction mixture.

This process is of particular interest because it efficiently produces the compound Id in spite of the presence in the starting quinazolinones of formula VIII of a carbonyl function with which the aryl magnesium halide or aryl lithium compound of formula IX would normally be expected to react under the conditions employed.

The reduction in process (g) may for example be effected with a borohydride, preferably an alkali metal borohydride such as sodium borohydride, with lithium aluminium hydride, or by hydrogenation in the presence of Raney nickel, platinum or palladium. The reduction is suitably carried out at a temperature of from 0° to 80°C, conveniently from 15° to 30°C. The organic solvent is preferably a lower alkanol such as methanol or ethanol, more preferably ethanol. Co-solvents such as methylene chloride, chloroform or water may be employed, if desired. When $R_1$ in the compounds of formula Ia signifies, a nitro-substituted phenyl group, reducing agents and/or conditions are, naturally, selected, whereby the nitro group is not reduced simultaneously with the double bond of the nucleus. Alkali metal borohydrides may, for example, be employed when a nitro group is present.

Process (h) is conveniently carried out at room temperature (approximately 20°C), or at elevated temperatures up to about 100°C. Suitable organic solvents which are inert under the reaction conditions include dimethylacetamide, diethylacetamide, dimethylformamide, dimethylsulfoxide and dioxane. Preferably the compound of formula X is a sodium or potassium salt, and the compound of formula XI is preferably an iodide.

Process (i) is suitably effected in an organic solvent which is inert under the reaction conditions and at least partially water-miscible, e.g. dioxane or acetone, at, e.g. room temperature (approximately 20°C), using for example an aqueous solution of sodium permanganate or potassium permanganate as the oxidising agent.

Process (j) is conveniently effected at a temperature of from 0° to 50°C, preferably 15° to 30°C. The process may suitably be carried out in the presence of an organic solvent which is inert under the reacting conditions, such as a lower alkanol e.g. methanol or ethanol.

Process (k) is preferably effected by alkaline hydrolysis of the compound of formula XV at a temperature of from 50° to 150°C, preferably 80° to 120°C. The preferred reagents for effecting the alkaline hydrolysis are alkali metal hydroxides such as sodium and potassium hydroxide. The reaction is conveniently carried out in an aqueous solvent medium comprising water and a water-miscible organic solvent which is inert under the reaction conditions, such as a lower alkanol, e.g. ethanol, or a cyclic ether, e.g. dioxane, and preferably dioxane.

Process (k) may also be effected by oxidative hydrolysis of the compound of formula XV, in an aqueous alkaline medium at a temperature of from 10° to 80°C, preferably 15° to 60°C. The oxidative hydrolysis is preferably effected in an alkaline medium employing a peroxide, preferably a hydroperoxide and more preferably hydrogen peroxide. The peroxide is preferably used in moderate excess, typically about 1.5 to 4 molar equivalent excess. An alkali metal hydroxide, e.g. sodium or potassium hydroxide, is suitable employed to provide the alkaline medium and is preferably employed in large excess. The alkaline oxidative hydrolysis is conveniently carried out in an aqueous solvent medium comprising water and an organic solvent which is inert under the reaction conditions, such as a lower alkanol or cyclic ether.

Process (l) is suitably carried out in an organic solvent which is inert under the reaction conditions at a temperature of from 0° to 60°C., preferably 15° to 40°C. The process is preferably effected in aqueous medium employing an oxidizing agent an aqueous solution of an alkali metal permanganate, such as sodium or potassium permanganate, more preferably the latter. The organic solvent may for example be an aromatic solvent such as benzene, or an acyclic or cyclic ether such as dioxane, or lower alkanol such as ethanol, or a lower ketone such as acetone.

Process (m) may be conveniently carried out in an inert organic solvent at temperatures in the range of 0°C. to 120°C., typically 15°C. to 100°C. The oxidizing agents which may be employed are of known type suitable for converting an organic amino moiety to an imino moiety. Representative of such oxidizing agents are the alkali metal permanganates, such as sodium or potassium permanganate, manganese dioxide and mercuric acetate. The permanganates are the preferred oxidizing agents. The organic solvent may be any of several conventional organic solvents including by way of illustration methylene chloride, the lower alkanols, methanol and ethanol, the aromatic solvents, e.g., benzene and the ethers including the cyclic ethers, e.g., dioxane. The product of formula If may be isolated from the reaction by working up by established procedures.

Process (n) is carried out at elevated temperatures in the range of 30° to 120°C., preferably 50° to 100°C. The reaction is suitably carried out in the presence of an acid as catalyst and dehydrating agent which is otherwise non-reactive with compounds XVII and XVIII, for example, an inorganic mineral acid, such as hydrochloric acid (hydrogen chloride in an aromatic solvent) or an organic acid such as trifluoroacetic acid, oxalic acid or an arylsulfonic acid an alkylsulfonic acid such as benzensulfonic acid, p-toluenesulfonic acid and methanesulfonic acid. The amount of acid catalyst is desirably controlled at a minor amount not substantially exceeding about one molar equivalent based on the compound XVII and is most preferably a minor equivalent based on the compound XVII and is most preferably a minor catalytic amount between 0.005 to 0.5 molar equivalent based on the urea. The conducting of the reaction under anhydrous or nearly anhydrous conditions is important to obtaining effective results. The reaction is conveniently carried out in an organic solvent which may be any of several conventional organic solvents providing an inert reaction medium, preferably an aromatic solvent such as benzene toluene and the like. Depending upon known factors such as reaction temperature, etc. the reaction may take typically between 1 to 50 hours. The reaction product of formula Tg may be isolated from the reaction mixture by working up by established procedures.

The resulting compounds of formula I may be isolated and purified using conventional techniques.

The compounds of formulae IV and IVa employed as starting materials in processes (a) and (b) may be produced by reacting a corresponding compound of formula V, stated above, with ammonia in a known manner. The reaction is desirably carried out in a sealed reactor under anhydrous conditions and at an elevated temperature and pressure. The reaction temperature is suitably from 100° to 200°C., preferably 110° to 150°C. A catalyst such as a Lewis acid, e.g. zinc chloride, may be employed to advantage in the process. The reaction is preferably carried out using an excess of ammonia as solvent, although a suitable co-solvent, e.g. dioxane, may also be employed.

The compounds of the formula IV having the formula IVb,

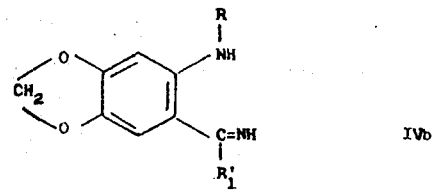

in which R and R₁' are as defined above, may also be produced by reacting a compound of formula XIX,

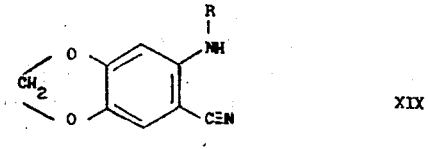

in which R is as defined above, with a compound of formula IX, stated above and hydrolyzing the resulting product in manner known per se.

The reaction of the compound of formula XIX with the compound IX is preferably effected at room temperature in an inert organic solvent, e.g. diethyl ether. The compound of formula IX is preferably a lithium compound. The resulting reaction mixture is suitably subjected directly to hydrolysis in manner known per se. The hydrolysis may suitably be effected for example by simply pouring the mixture over ice.

The compounds of formula V and Va employed as starting materials in processes (c) and (d), and in producing compounds IV and IVa, as described above, are either known, or may be produced in conventional manner from available materials.

The compounds of formula VII, employed as starting materials in process (e), may be produced by reacting a compound of formula XX,

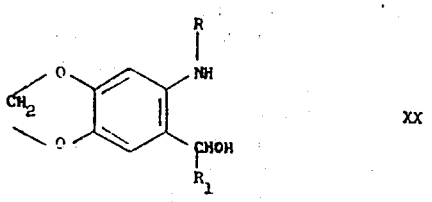

in which R and $R_1$ are as defined above,
with isocyanic acid.

The reaction is desirably carried out in acidic aqueous medium at a controlled temperature of from 0° to about 80°C., preferably from 15° to 35°C. The isocyanic acid is preferably formed in situ by effecting the reaction in acidic medium and employing a salt of isocyanic acid of formula VI, stated above. The compound of formula VI is suitably an alkali metal, e.g. sodium or potassium, an alkaline earth metal, e.g. calcium, or ammonium isocyanate and is preferably potassium isocyanate. The acid employed to provide the acidic reaction medium and produce in situ the desired isocyanic acid from the salt of formula VI is preferably a strong inorganic acid, for example, sulfuric acid or hydrochloride acid, or an organic acid such as acetic acid, more preferably the latter.

The compounds of formula VIII, employed as starting materials in process (f), may be produced reacting a compound of formula XXI,

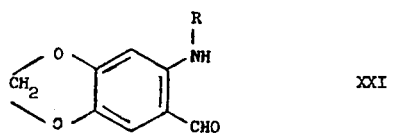

in which R is as defined above,
with urea at an elevated temperature.

The reaction is most suitably effected at a temperature of from 50° to 250°C., preferably 100° to 200°C. The reaction is conveniently carried out in the absence of a solvent in an inert atmosphere such as nitrogen gas. The reaction may also be carried out in an organic solvent which is inert under the reaction conditions, for example, an aromatic solvent such as benzene or toluene.

The compounds of formula X used as starting materials in process (h) may readily be obtained by treating the corresponding 1-unsubstituted quinazolinone in manner known per se for the preparation of such alkali metal salts, e.g. with sodium hydride or an alkali metal alkoxide such as sodium methoxide, sodium ethoxide, potassium methoxide or potassium ethoxide. The reaction is suitably carried out at room temperature in an organic solvent which is inert under the reaction conditions, e.g. dimethylacetamide, diethylacetamide, dimethylformamide, dimethylsulfoxide or dioxane. Suitably the same solvent is used for the subsequent preparation of compounds of formula Ib.

The 1-unsubstituted quinazolinones themselves are novel and can be prepared in a known manner from known type materials, for example, by process (c)(i) or (ii), described above, from the appropriate 2-aminobenzophenone, i.e. a compound of formula V wherein R is hydrogen.

The compounds of formula XII, employed as starting materials in process (i), may be obtained by reacting a compound of formula XXII,

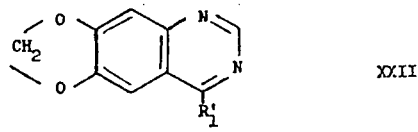

in which $R_1'$ is as defined above,
with a compound of formula XXXII,

in which X' is as defined above,
at a temperature from about room temperature (approximately 20°C.) to about 45°C., there being employed either an excess of the compound of formula XXIII or an organic solvent which is inert under the reaction conditions, e.g. chloroform or acetone, as reaction medium.

Preferably the reaction is commenced at room temperature, e.g. for 1 to 4 hours, and then continued at reflux temperature, using an excess of methyl iodide. When there is used a compound of formula XXIII, which is a gas at room temperature, it is of course desirable to use an organic solvent as reaction medium.

The compounds of formula XIII employed as starting material in process (i) may be produced by reducing a compound of formula XII, stated above. The reduction is suitably carried out using a borohydride, e.g. sodium borohydride, as reducing agent, conveniently in the presence of an organic solvent which is inert under the reaction conditions, e.g. a lower alkanol such as methanol or ethanol, or a mixture of a lower alkanol with methylene chloride, chloroform or water. The reduction is desirably carried out at a temperature of from about room temperature (approximately 20°C.) to about 80°C. The resulting compound of formula XIII may be isolated and purified by conventional techniques. However, in general, it has a tendency to be somewhat unstable and, therefore, if it is to be used to prepare a compound of formula Ie it is desirable to oxidize it as soon as possible.

The compounds of the formula XIV, employed as starting material in process (j) may be prepared by reacting a compound of the formula V, stated above, with trihalogen acetic acid of the formula XXIV,

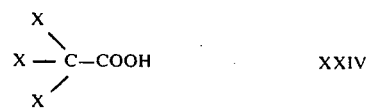

in which X is as defined above,
or with a reactive derivative thereof.

The process is suitably effected at a temperature of from minus 20° to plus 20°C., and in an inert organic solvent, e.g. an aromatic solvent, such as benzene.

The compounds of the formula XV used as a starting material in process (k) are preferably prepared by oxidizing a compound of the formula XVI stated above under substantially anhydrous conditions. Suitable temperatures are in the range of 0° to 150°C. with 20° to 60°C. being preferred. Any oxidizing agent suitable for converting an organic amino moiety to an imino moiety can be used, for example, alkali metal permanganates, mercuric acetate and preferably manganese dioxide which has been maintained free of moisture. Solvents which can be used include aromatic solvents such as benzene and toluene as well as other inert organic solvents such as acyclic or cyclic ethers, e.g. dioxane.

The compounds of the formula XIV employed as starting material in process (l) and in the preparation of compounds of the formula XV may be prepared by reacting a compound of the formula XXV,

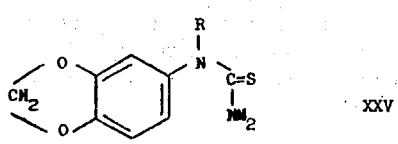

XXV in which R is as defined above,
with a compound of the formula XVIII, above, at elevated temperatures in the presence of an acid as catalyst. This reaction is carried out at elevated temperatures in the range of 30°C. to 120°C. preferably 50°C. to 100°C. The reaction is suitably carried out in the presence of an acid as catalyst and dehydrating agent but which is otherwise nonreactive with compounds XXV and XVIII, for example, an inorganic mineral acid such as hydrogen chloride or an organic acid such as trifluoroacetic acid or an arylsulfonic acid or an alkylsulfonic acid such as benzenesulfonic acid, p-toluenesulfonic acid and methanesulfonic acid. The amount of acid catalyst is not critical but desirably controlled at a minor amount not substantially exceeding about one mole based on the compound XXV, and is most preferably a minor catalytic amount between up to 0.5 mole per mole of compound XXV. The conducting of the reaction under anhydrous or nearly anhydrous conditions is important to obtaining effective results. The reaction is conveniently carried out in an organic solvent which may be any of several conventional organic solvents providing an inert reaction medium, preferably an aromatic solvent such as benzene and the like. Depending upon known factors such as reaction temperature, etc. the reaction may take typically between 1 to 50 hours. The reaction product of formula XVI may be isolated from the reaction mixture by working up by established procedures.

The compounds of the formula XVII are preferably prepared by subjecting a compound of the formula XXVI,

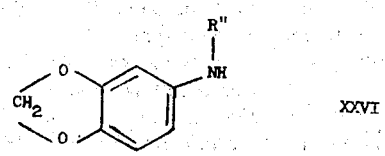

XXVI wherein R" is as defined, to reaction with isocyanic acid which is provided in a conventional manner by forming in-situ from an alkali metal isocyanate (also obtainable and known as alkali metal cyanates) and a suitable acid such as a lower aliphatic carboxylic acid, preferably acetic acid. The reaction may be suitably carried out at temperatures in the range of 10° to 50°C. and in an organic solvent medium which may be conveniently a lower aliphatic carboxylic acid such as excess acetic acid.

The compounds of formula XVII may also be provided starting with a compound of formula XXVI by subjecting the latter to reaction with nitrourea at temperatures typically in the range of 80° to 120°C. in an inert organic solvent of conventional type, preferably a lower alkanol such as ethanol.

Compounds of formula XVIII are known and can be prepared from known materials using conventional procedures.

The compounds of formula XIX, used for producing compounds of formula IVb as described above, may be produced in manner know per se by tosylation, alkylation and detosylation of a compound of formula XXVII,

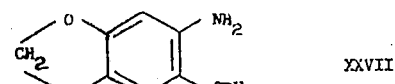

XXVII

Compounds of formula XIXa

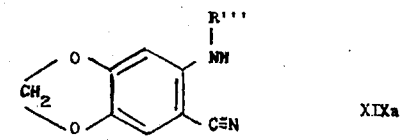

XIXa in which R''' signifies cycloalkyl or a branched alkyl radical of 3 to 5 carbon atoms, in which the branching occurs on the carbon atom adjacent to the nitrogen atom,
are, however, preferably produced by reacting a compound of formula XXVII, stated above, with a compound of formula XXVIII,

R''' — X"    XXVIII in which R''' is as defined above, and X" is bromo or iodo, preferably iodo.

The reaction is desirably carried out in the presence of a base, preferably an inorganic base, such as an alkali metal carbonate, to take up the hydrogen halide liberated during the reaction. The reaction may be effected in an organic solvent which is inert under the reaction conditions, e.g. dioxane, benzene and toluene. However, the use of a solvent is not necessary and a substantial excess of the compound of formula XXVIII is preferably employed to provide the solvent medium. The reaction is suitably carried out at an elevated temperature which is not especially critical but preferably lies in the range of from 60° to 140°C., more preferably 70° to 110°C.

The compound of formula XXVII is known.

The compounds of formula XX used for producing compounds of formula VII, as described above, may be produced in manner known per se, e.g. by reduction of a compound of formula V, stated above, for example with sodium borohydride, in an organic solvent which is inert under the reaction conditions, as described by G. N. Walker, J. Org. Chem. 27, 1929 (1962).

The compounds of formula XXI used for producing compounds of formula VIII, as described above, may be produced in manner known, for example, by reducing a compound of the formula XIX with a suitable catalyst, e.g. Rancy Nickel/aluminum alloy, in the presence of an acid, e.g. formic acid, at elevated temperatures suitably in the range of 40°C. to 100°C. in a liquid medium which may be provided by employing an excess of the acid.

The compounds of the formula XXII, employed for producing compounds of formula XII, as described, may be produced in manner known per se. For example, compounds of formula XXII, above, may be produced by oxidation of a compounds of formula XXIX,

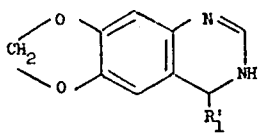

in which $R_1'$ is as described above.

The oxidation is suitably carried out in manner analogous to process (i), described above.

The compounds of formula XXIX may be produced by reacting a compound of formula XXX,

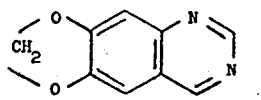

with a compound of formula IX, stated above, in a manner analogous to process (f), above.

The compound of the formula XXX is known. The compounds of formula XXV may be suitably prepared by subjecting a compound of the formula XXXI,

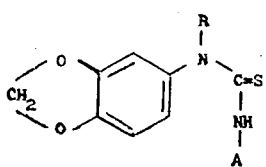

wherein R is as defined and A is the residue of an acid halide, to alkaline hydrolysis at elevated temperatures in the range of 50°C. to 140°C., preferably 80° to 120°C.

The hydrolysis is suitably effected employing an alkali metal hydroxide, preferably sodium or potassium hydroxide. The reaction is carried out in a suitable liquid solvent medium preferably comprising water and a water miscible inert organic solvent of conventional type such as an ether, including the cyclic ethers, preferably dioxane.

The reaction product of formula XXV may be isolated from the aforementioned reaction by working up by conventional procedures.

The compounds of formula XXVI are either known or can be prepared from known materials by established procedures. A preferred method of preparation of compounds XXVI employes as starting material a compound of formula XXXII

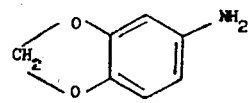

and involves subjecting said compound XXXII to known type protection reactions such as to reaction with a trialkylorthoformate followed by treatment with a strong acid such as sulfuric acid or to tosylation, alkylation and detosylation, all in a manner known per se. It will be noted that compounds XXVI in which R'' is a cycloalkyl or branched alkyl with the branching occurring on the carbon atom attached to amino nitrogen may be most conveniently and preferably prepared by reacting directly compound XXXII with the appropriate alkyl halide.

The compounds of the formula XXXI may be prepared by subjecting a compound of the formula XXVI, above, to reaction with an isothiocyanate of formula XXXIII $$M-N=C=S \qquad \text{XXXIII}$$

wherein M is a cation, and an acid halide of the formula XXXIV $$AX'''' \qquad \text{XXXIV}$$

wherein A is as previously indicated and $X''''$ is halogen, preferably chloro, or to the action of the reaction product of said acid halide and isothiocyanate.

The preparation of compounds XXXI from a compound XXVI is conveniently carried out in an inert solvent medium at temperatures in the range of 10° to 80°C., preferably 30° to 70°C. The reaction may be understood as including the reaction of compound XXVI with the reaction product of the acid halide of formula XXXIV and isothiocyanate of formula XXXIII. For this reason, it is generally preferred to first react the acid halide and isothiocyanate and then add the starting compound XXVI to the resulting reaction mixture. The reaction of the acid halide and isothiocyanate is preferably inititated at lower temperatures in the range of 10° to 40°C. As acid halides one employs any of the conventional acid halides which do not carry substituents or functional groups leading to undesired reactions. The more suitable materials are represented, for example, by acetyl chloride and benzoyl chloride, preferably benzoyl chloride. The preferred isothiocyanates are those most readily reacting with the acid halide to eliminate as by-product a halide of the cation M. The preferred cations M may be represented, for example, by a cation of an alkali metal, e.g., sodium, and by the cation of ammonia, e.g., the ammonium salt. The more preferred isothiocyanate is ammonium isothiocyanate. Organic solvents suitable for the reaction are of conventional type which provide an inert medium. Such solvents include, by way of example, benzene, the lower alcohols, ketones and cyclic ethers, preferably acetone. The reaction product of formula XXXI may be recovered from the reaction by working up by conventional procedures. It will also be noted that in going from compound XXVI to compound XXV complete isolation and/or recovery of the intermediate compound XXXI is not necessary, and that in certain cases the reaction mixtures from the reaction of compounds XXVI and XXXIII may contain varying amounts of the compound of formula XXV.

The compound of formula XXXII can be prepared from known materials by established procedures, for example, by subjecting methylenedioxybenzene to nitration to obtain a 3,4-methylenedioxynitrobenzene which is then subjected to catalytic reduction with hydrogen employing a platinum oxide or palladium on charcoal as catalyst to obtain said compound of formula XXXII.

The compounds of the formula XVI in which $R_1$ is $R_1'$, as above defined may also be prepared by reacting a compound of the formula XXXV

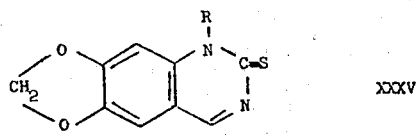

XXXV in which R is as defined above,
with a compound of the formula IX above stated in a manner analogous to process (f), above described.

The compounds of the formula XXXV may be obtained in a manner analogous to that above-described for the preparation of the compounds of the formula VIII by reacting a compound of the formula XXI with thiourea.

Unless otherwise indicated, the products of the various intermediary processes described herein, may be isolated and purified using conventional techniques.

The compounds of formula I are useful because they possess pharmaceutical activity in animals. In particular, the compounds are useful as anti-inflammatory agents as indicated by the Carrageenan-induced edema test in rats. For such use, the compounds may be combined with a pharmaceutically acceptable carrier, and such other conventional adjuvants as may be desired, and preferably administered orally in such forms as tablets, capsules, elixirs, suspensions and the like. For the above-mentioned use, the dosage administered will, of course, vary depending upon known factors such as the particular compound used and mode of administration. However, in general, the compounds of formula Ia provide satisfactory results when administered at a daily dose of from about 0.15 milligrams to 180 milligrams per kilogram of body weight, preferably given in divided doses 2 to 4 times a day, with daily dosage for large mammals ranging from between about 10 milligrams to 1000 milligrams and individual doses between 3 milligrams to 500 milligrams. The compounds of formula Ic in general provide satisfactory results when administered at a daily dose of from about 2 milligrams to 200 milligrams per kilogram of body weight, preferably given in divided doses, with daily dose for large mammals ranging between about 140 milligrams to 2000 milligrams and individual doses ranging between 35 to 1000 milligrams.

The compounds of the formula I, particularly Ia, are also useful as analgesics, as indicated by application of pressure to yeast-inflamed foot of the rat (oral administration), and as anti-pyretics as indicated by inhibition of yeast-induced fever in rats (oral administration). For such uses, the compounds may be administered in modes and forms similar to those employed in the treatment of inflammation and at dosages indicated above as applicable for the use of the compound in the treatment of inflammation.

The compounds may be administered orally in such forms as tablets, dispersible powders, granules, capsules, elixirs, suspensions and syrups, or parenterally in the form of an injectable solution or suspension. Such compositions may be prepared according to any method known in the art for the manufacture of pharmaceutical compositions, and such compositions may contain one or more conventional adjuvants, such as sweetening agents, flavoring agents, coloring agents and preserving agents, in order to provide an elegant and palatable preparation. Tablets may contain the active ingredient in admixture with conventional pharmaceutical excipients, e.g., inert diluents such as calcium carbonate, sodium carbonate, lactose and talc, granulating and disintegrating agents, e.g., starch and alginic acid, binding agents, e.g., magnesium stearate, stearic acid and talc. The tablets may be uncoated or coated by known techniques to delay disintegration and adsorption in the gastro-intestinal tract and thereby provide a sustained action over a longer period. Similarly, suspensions, syrups and elixirs may contain the active ingredient in admixture with any of the conventional excipients utilized for the preparation of such compositions, e.g., suspending agents (methylcellulose, tragacanth and sodium alginate), wetting agents (lecithin, polyoxyethylene stearate and polyoxyethylene sorbitan monooleate) and preservatives (ethyl-p-hydroxy-benzoate). Capsules may contain the active ingredient alone or admixed with an inert solid diluent, e.g., calcium carbonate, calcium phosphate and kaolin.

The preferred pharmaceutical compositions from the standpoint of preparation and ease of administration are solid compositions, particularly hard-filled capsules and tablets.

A representative formulation is a capsule prepared by conventional techniques and containing the following ingredients:

| Ingredient | Parts by Weight |
|---|---|
| Compound of formula I, e.g. 1-isopropyl-4-phenyl-6,7-methylenedioxy-2(1H)-quinazolinone | 50 |
| Inert solid diluent e.g. Kaolin | 200 |

Preferred compounds of formula I from the point of view of pharmacological activity, are the compounds of formula Ia, particularly those in which H signifies an isopropyl radical, for example, 1-isopropyl- 4-phenyl-6,7-methylenedioxy-2(1H)-quinazolinone and 1-isopropyl-4-(p-fluorophenyl)- 6,7-methylenedioxy-2(1H)-quinazolinone.

The intermediates of the formula XVII are also useful because they exhibit pharmacological activity in animals. In particular, the compounds of the formula XVII are useful as anti-inflammatory agents as indicated by the Carrageenan-induced edema test in rats. Such compounds, which may be administered in modes and forms similar to the compounds of formula I, generally provide satisfactory anti-inflammatory results when administered at a daily dose of from 2 to 200 milligrams per kilogram of animal body weight with daily dosage for large mammals being in the range between about 140 to 2000 milligrams and divided doses between 35 and 1000 milligrams.

As used herein, the expression "in manner known per se" means methods in use or described in the literature on the subject.

The following examples illustrate the invention. Unless otherwise indicated, percentages are by weight and temperatures are in degrees Centigrade.

EXAMPLE A

Preparation of 2-isopropylamino-4,5-methylenedioxy benzophenone

Step 1

To a flask equipped with a stirrer and Dean-Stark water separator are charged 53g. of benzoin, 51g. of 3,4-methylenedioxyaniline, 2.5g. of p-toluenesulfonic acid and 300 ml. of xylene. The mixture is stirred and refluxed for 10 hours. After cooling to room temperature 1500 ml of chloroform are added and the organic layer is washed two times with 150 ml. of 10%, sulfuric acid. The organic layer is treated with charcoal, filtered and concentrated in vacuo to ca. 500 ml. On standing there is obtained 2,3-diphenyl-5,6-methylenedioxyindole, m.p. 187°–188°C.

Step 2

To a flask equipped with a stirrer, condenser, dropping funnel and thermometer are charged 31.3 g. of 2,3-diphenyl-5,6-methylenedioxy indole, 600 ml. of acetic acid and 0.30 g. of ammonium molybdate dissolved in 30 ml. of water. The stirred mixture is heated to 60°–65°C. and then treated dropwise (about 15 minutes) with 30 ml. of 40% hydrogen peroxide. The mixture is maintained at 65° for about 2 hours and then treated with 150 ml. water. The resultant solid is filtered off and recrystallized from chloroform to give 2-benzoylamino-4,5-methylenedioxybenzophenone, m.p. 195°–197°C.

Step 3

To a flask equipped with a stirrer and condenser are charged 40 g. of 2-benzoylamino-4,5-methylenedioxybenzophenone, 150 ml. of ethanol and 100 ml. of 50% sodium hydroxide. The mixture is stirred and refluxed for 2 hours. The solution is treated with 400 ml. of water and the resulting solid is filtered off to give 2-amino-4,5-methylenedioxybenzophenone m.p. 160°–161°C.

Step 4

To a flask equipped with a stirrer and condenser are charged 80 g. of 2-amino-4,5-methylenedioxybenzophenone, 600 ml. of isopropyliodide and 80 g. anhydrous potassium carbonate. The mixture is stirred and refluxed for ca. 48 hours, cooled to room temperature, filtered and concentrated in vacuo on a rotary evaporator. The residue is dissolved in 1:1 chloroform-hexane and chromatographed through a silica gel (500 g.) column with the same solvent system. There is obtained 2-isopropylamino-4,5-methylenedioxybenzophenone, which, when recrystallized from ethanol, has a melting point of 77–78°C.

EXAMPLE 1

Process (C) (i)

Preparation of 1-isopropyl-4-phenyl-6,7-methylenedioxy-2(1H)quinazolinone

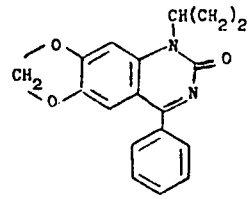

To a flask equipped with a stirrer and a condenser-distillation head arranged for atmospheric distillation are charged 28 g. of 2-isopropylamino-4,5-methylenedioxybenzophenone (prepared as in Example A), 50 g. of ethyl carbamate and 4.5 g. of anhydrous zinc chloride. The mixture is stirred and heated at 160°–165°C. for 45 minutes; 175°–180°C. for 45 minutes and 185°–190°C. for 1.0 hour. During this period a distillate of ethanol and ethyl carbamate is obtained. The cooled residue is treated with ca. 250 ml. chloroform and 25 g. of charcoal. The mixture is filtered and the filtrate concentrated in vacuo. The residue is dissolved in 1:1 chloroform-hexane and chromatographed through a silica gel (150 g.) column with the same solvent system. There is obtained 1-isopropyl-4-phenyl-6,7-methylenedioxy- 2(1H)-quinazolinone, m.p. 194°–194.5°C.

EXAMPLE B

Preparation of 2-(N-carbamoylisopropylamino)-4,5-methylenedioxybenzhydrol)

Step 1

To a flask equipped with a stirrer and condenser are charged 5.09 g. of 2-isopropylamino-4,5-methylenedioxybenzophenone (prepared in Example A) and 125 ml. of methanol. The stirred solution is treated portionwise (ca. 15 minutes) with 2.5 g. of sodium borohydride. The resulting mixture is stirred at room temperature for ca. 12 hours and then concentrated in vacuo. The residue is treated with 100 ml. of water and then extracted with two 50 ml. portions of $CH_2Cl_2$. The organic layer is dried with anhydrous $Na_2SO_4$, filtered and concentrated. Upon recrystallization from ether, there is obtained 2-isopropylamino-4,5-methylenedioxybenzohydrol, which melts at 78°–80°C.

Step 2

To a flask equipped with stirrer are charged 1.5 g. of 2-isopropylamino-4,5-methylenedioxybenzhydrol and 7.5 ml. of 2N HCl. The solution is stirred and treated in one portion with 0.78 g. of sodium cyanate in 15 ml. of water. After stirring for ca. 18 hours at room temperature the reaction mixture is filtered and the obtained solids recrystallized from ether to give 2-(N-carbamoylisopropylamino)-4,5-methylene-dioxybenzhydrol, m.p. 145°–150°C. (ether).

EXAMPLE 2

Process (e)

Preparation of 1-isopropyl-4-phenyl-6,7-methylenedioxy-3,4-dihydro-2(1H)-quinazolinone

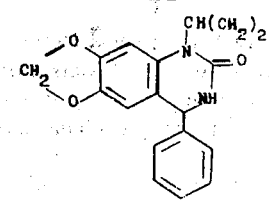

Example B, Step 2 is repeated except that the reaction mixture is refluxed for 2 hours to obtain 1-isopropyl-4-phenyl-6,7-methylenedioxy-3,4-dihydro-2(1H)-quinazolinone having a melting point of 165°–168°C. when recrystallized from a mixture of ether and isopropanol.

EXAMPLE 3

Process (g)

Preparations of 1-isopropyl-4-phenyl-6,7-methylenedioxy-3,4-dihydro-2(1H)-quinazolinone To a flask equipped with stirrer and condenser are charged 10.29 g. of 1-isopropyl-4-phenyl-6,7-methylenedioxy-2-(1H)-quinazolinone and 250 ml. of methanol. The stirred solution is treated portion-wise (ca. 30 minutes) with 5.0 g. of sodium borohydride. The reaction is stirred for 5 hours at room temperature and then concentrated in vacuo on a rotary evaporator. The residue is treated with 200 ml. of water and then extracted 2 times with $CH_2Cl_2$. The organic layer is dried with anhydrous $Na_2SO_4$, filtered and concentrated in vacuo. There is obtained 1-isopropyl-4-phenyl-6,7-methylene- dioxy-3,4-dihydro-2(1H)-quinazolinone, melting at 161°–163°C. upon recrystallization from ether.

EXAMPLE C

Preparation of 2-(N-trifluoroacetylisopropylamino)-4,5-methylenedioxy benzophenone To a flask equipped with stirrer, thermometer, dropping funnel and an anhydrous calcium chloride drying tube are charged 3.0 g. of 2-isopropylamino-4,5-methylenedioxybenzophenone (prepared in Example A), 1.43 g. triethylamine and 30 ml. of dry toluene. The stirred solution is cooled to an internal temperature of about 10°C. and treated dropwise with a solution of 2.4 g. trifluoroacetic anhydride in 10 ml. of toluene at such a rate that the internal temperature is 10°±5°C. The mixture is then allowed to come to room temperature and after ca. 12 hours is washed with 100 ml. water, dried with anhydrous $MgSO_4$, filtered and concentrated. There is obtained 2-(N-trifluoroacetylisopropylamino)-4,5-methylenedioxybenzophenone, melting at 100°–102°C. upon recrystallization from ether.

EXAMPLE 4

Process (j)

Preparation of 1-isopropyl-4-phenyl-6,7-methylenedioxy-2(1H)-quinazolinone

A mixture of 1.0 g. of 2-(N-trifluoroacetylisopropylamino)-4,5-methylenedioxybenzophenone (prepared as in Example C) and 50 ml. of tetrahydrofuran saturated with anhydrous ammonia is stirred at room temperature for 48 hours. The solvent is removed in vacuo and the residue recrystallized from isopropanol to give 1-isopropyl-4-phenyl-6,7-methylenedioxy-2(1H)-quinazolinone, m.p. 189°–190°C.

Following substantially the procedure of the foregoing examples the following compounds of the invention are prepared:

A-1. 1-isopropyl-4-(m-fluorophenyl)-6,7-methylenedioxy-3,4-dihydro-2(1H)-quinazolinone, m.p. 165°–167°C.

A-2. 1-isopropyl-4-(m-fluorophenyl)-6,7-methylenedioxy-2(1H)-quinazolinone, m.p. 169°–170°C.

B-1. 1-isopropyl-4-(m-methoxyphenyl)-6,7-methylenedioxy-3,4-dihydro-2(1H)-quinazolinone, m.p. 167°–168°C.

B-2. 1-isopropyl-4-(m-methoxyphenyl)-6,7-methylenedioxy-2(1H)-quinazolinone, m.p. 189°–191°C.

C-1. 1-isopropyl-4-(p-methylphenyl)-6,7-methylenedioxy-3,4-dihydro-2(1H)-quinazolinone, m.p. 192°–194°C.

C-2. 1-isopropyl-4-(p-methylphenyl)-6,7-methylenedioxy-2(1H)-quinazolinone, m.p. 188°–190°C.

D-1. 1-isopropyl-4-(o-nitrophenyl)-6,7-methylenedioxy-3,4-dihydro-2(1H)-quinazolinone, m.p. 202°–205°C.

D-2. 1-isopropyl-4-(o-nitrophenyl)-6,7-methylenedioxy-2(1H)-quinezolinone, m.p. 148°–150°C.

E-1. 1-isopropyl-4-(5'-chloro-2-thienyl)-6,7-methylenedioxy-3,4-dihydro-2(1H)-quinazolinone, m.p. 162°–164°C.

E-2. 1-isopropyl-4-(5'-chloro-2-thienyl)-6,7-methylenedioxy-2(1H)-quinazolinone, m.p. 192°–201°C.

F-1. 1-isopropyl-4-(3,4-methylenedioxyphenyl)-6,7-methylenedioxy-3,4-dihydro-2(1H)-quinazolinone, m.p. 145°–147°C.

F-2. 1-isopropyl-4-(3,4-methylenedioxyphenyl)-6,7-methylenedioxy-2(1H)-quinazolinone, m.p. 234°–235°C.

G-1. 1-isopropyl-4-(m-nitrophenyl)-6,7-methylenedioxy-3,4-dihydro-2(1H) -quinazolinone, m.p. 218°–220°C.

G-2. 1-isopropyl-4-(m-nitrophenyl)-6,7-methylenedioxy-2(1H)-quinazolinone, m.p. 230°–232°;

H-1. 1-isopropyl-4-(o-methylphenyl)-6,7-methylenedioxy-3,4-dihydro-2(1H)-quinazolinone, m.p. 172°–174°;

H-2. 1-isopropyl-4-(o-methylphenyl)-6,7-methylenedioxy-2(1H)-quinazolinone, m.p. 155°–157°;

I-1. 1-isopropyl-4-(p-fluorophenyl)-6,7-methylenedioxy-3,4-dihydro-2(1H)-quinazolinone, m.p. 163°–166°;

I-2. 1-isopropyl-4-(p-fluorophenyl)-6,7-methylenedioxy-2(1H)-quinazolinone, m.p. 238°–240°;

J-1. 1-isopropyl-4-(3,4-dichlorophenyl)-6,7-methylenedioxy-3,4-dihydro-2(1H)-quinazolinone, m.p. 155°–157°;

J-2. 1-isopropyl-4-(3,4-dichlorophenyl)-6,7-methylenedioxy-2(1H)-quinazolinone, m.p. 239°–242°;

K-1. 1-methyl-4-phenyl-6,7-methylenedioxy-3,4-dihydro-2(1H)-quinazolinone, m.p. 231°–232°;

K-2. 1-methyl-4-phenyl-6,7-methylenedioxy-2(1H)-quinazolinone, m.p. 257°–260°;

L-1. 1-cyclopropylmethyl-4-phenyl-6,7-methylenedioxy-3,4-dihydro-2(1H) -quinazolinone.

L-2. 1-cyclopropylmethyl-4-phenyl-6,7-methylenedioxy-2(1H)-quinazolinone.

What is claimed is:

1. A compound of the formula:

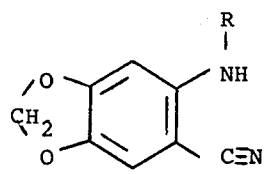
wherein R is alkyl of 1 to 5 carbon atoms, cycloalkyl of 3 to 6 carbon atoms, or cycloalkylalkyl of 4 to 7 total carbon atoms in which the cycloalkyl is of 3 to 6 carbon atoms and the alkyl is straight chain alkyl of 1 to 3 carbon atoms.
* * * * *